United States Patent
Park et al.

(10) Patent No.: US 11,382,520 B2
(45) Date of Patent: Jul. 12, 2022

(54) BLOOD PRESSURE MEASURING APPARATUS AND BLOOD PRESSURE MEASURING METHOD

(71) Applicant: SAMSUNG ELECTRONICS CO., LTD., Suwon-si (KR)

(72) Inventors: Sang Yun Park, Hwaseong-si (KR); Jae Min Kang, Seoul (KR); Yong Joo Kwon, Yongin-si (KR); Youn Ho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 552 days.

(21) Appl. No.: 16/296,444

(22) Filed: Mar. 8, 2019

(65) Prior Publication Data
US 2019/0274555 A1    Sep. 12, 2019

(30) Foreign Application Priority Data
Mar. 12, 2018   (KR) .................. 10-2018-0028759

(51) Int. Cl.
*A61B 5/021*       (2006.01)
*A61B 5/0225*     (2006.01)
(Continued)

(52) U.S. Cl.
CPC ...... *A61B 5/02116* (2013.01); *A61B 5/02255* (2013.01); *A61B 5/02007* (2013.01);
(Continued)

(58) Field of Classification Search
CPC ... A61B 5/021; A61B 5/0225; A61B 5/02255; A61B 5/02116; A61B 5/6826; A61B 5/02225; A61B 2562/0247; A61B 5/02007
See application file for complete search history.

(56) References Cited

U.S. PATENT DOCUMENTS 7,127,376 B2 * 10/2006 Nashner ............... A61B 5/1036
                                                        702/185
8,800,377 B2    8/2014 Kim
(Continued)

FOREIGN PATENT DOCUMENTS

| KR | 10-0497013 B1 | 6/2005 | |
| KR | 10-2009-0075537 A | 7/2009 | |
| WO | WO-2017152098 A1 * | 9/2017 | ......... A61B 5/02141 |

*Primary Examiner* — Eric J Messersmith
(74) *Attorney, Agent, or Firm* — Sughrue Mion, PLLC

(57) ABSTRACT

A blood pressure measuring apparatus according to an aspect of the present invention includes: a touch sensor; a pulse wave measurer configured to measure pulse waves from a user; a contact force measurer including at least three force sensors and configured to measure a contact force between the touch sensor and the user by using the at least three force sensors; a contact area measurer configured to measure a contact area between the user and the touch sensor; and a processor configured to determine a vertical direction error, which indicates a degree of deviation of a direction of force, applied by the user to press the touch sensor, from a vertical direction to a surface of the touch sensor based on sensor values sensed by the at least three force sensors, and estimate blood pressure according to a determination result of the vertical direction error based on the pulse waves, the contact force, and the contact area.

12 Claims, 15 Drawing Sheets

(51) Int. Cl.
    *A61B 5/00*          (2006.01)
    *A61B 5/022*        (2006.01)
    *A61B 5/02*          (2006.01)

(52) U.S. Cl.
    CPC ......... *A61B 5/02225* (2013.01); *A61B 5/6826* (2013.01); *A61B 2562/0247* (2013.01)

(56) References Cited

U.S. PATENT DOCUMENTS

| | | |
|---|---|---|
| 2007/0167844 A1 | 7/2007 | Asada et al. |
| 2009/0177096 A1 | 7/2009 | Kim |
| 2010/0298655 A1 | 11/2010 | McCombie et al. |
| 2010/0324384 A1 | 12/2010 | Moon et al. |
| 2011/0087112 A1* | 4/2011 | Leo ........................ A61B 90/98 600/478 |
| 2012/0190944 A1 | 7/2012 | Thaveeprungsriporn et al. |
| 2013/0296714 A1* | 11/2013 | Kassim .............. G01N 21/3151 600/479 |
| 2013/0310659 A1 | 11/2013 | Kawachi et al. |
| 2014/0198071 A1* | 7/2014 | Algreatly ............ G06F 3/04142 345/173 |
| 2014/0323886 A1 | 10/2014 | Lee et al. |
| 2014/0330087 A1 | 11/2014 | Succi et al. |
| 2015/0062078 A1* | 3/2015 | Christman ........... A61B 5/6897 345/174 |
| 2017/0245769 A1 | 8/2017 | Niehaus et al. |
| 2017/0251935 A1 | 9/2017 | Yuen |
| 2018/0177413 A1 | 6/2018 | Kwon et al. |

\* cited by examiner

BLOOD PRESSURE MEASURING APPARATUS AND BLOOD PRESSURE MEASURING METHOD

CROSS-REFERENCE TO RELATED APPLICATION(S)

This application claims priority from Korean Patent Application No. 10-2018-0028759, filed on Mar. 12, 2018, in the Korean Intellectual Property Office, the disclosure of which is incorporated herein by reference in its entirety.

BACKGROUND

1. Field

Apparatuses and methods consistent with exemplary embodiments relate to cuffless blood pressure monitoring.

2. Description of the Related Art

A pressurized cuff is generally used for measuring blood pressure. A blood pressure measuring method utilizing the pressurized cuff is a non-continuous measuring method, in which the cuff is inflated so that an artery is constricted up to around systolic blood pressure, and then the pressure in the cuff is slowly released. However, the pressurized cuff includes a booster pump and the like, such that the cuff is unsuitable for use in a mobile device.

Recently, research is being conducted on a method of cufflessly measuring blood pressure in a non-pressure manner without using a cuff, and examples thereof include a blood pressure measuring apparatus using Pulse Transit Time (PTT) and a blood pressure measuring apparatus using Pulse Wave Analysis (PWA). However, the blood pressure measuring apparatus using PTT is inconvenient in that correction is required for each user to ensure accuracy of measurement; and since bio-signals should be measured at two or more locations to measure the pulse wave velocity, the apparatus cannot be manufactured in a compact size. Further, the blood pressure measuring apparatus using PWA estimates blood pressure by analyzing only a pulse wave form, such that the apparatus is vulnerable to noise, and blood pressure may not be measured with improved accuracy.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide an apparatus and a method for cufflessly measuring blood pressure with improved accuracy.

According to an aspect of an exemplary embodiment, there is provided a blood pressure measuring apparatus including: a touch sensor; a pulse wave measurer configured to measure pulse waves from a user; a contact force measurer including at least three force sensors and configured to measure a contact force between the touch sensor and the user by using the at least three force sensors; a contact area measurer configured to measure a contact area between the user and the touch sensor; and a processor configured to determine a vertical direction error, which indicates a degree of deviation of a direction of force, applied by the user to press the touch sensor, from a vertical direction to a surface of the touch sensor based on sensor values sensed by the at least three force sensors, and estimate blood pressure of the user according to a determination result of the vertical direction error based on the pulse waves, the contact force, and the contact area.

The pulse waves may include photoplethysmography.

The at least three force sensors may be disposed around the pulse wave measurer and positioned at a center of the at least three force sensors The at least three force sensors may be disposed at an equal distance from the pulse wave measurer.

The contact force measurer may measure the contact force between the user and the touch sensor by adding up or averaging the sensor values sensed by the at least three force sensors.

The processor may calculate dispersion of the sensor values sensed by the at least three force sensors, and may determine the vertical direction error based on the calculated dispersion.

The processor may determine that the vertical direction error increases as the calculated dispersion increases.

The processor may generate a vertical direction error vector, which indicates the direction of the force applied by the user to press the touch sensor, and the degree of the deviation of the direction of force from the vertical direction to the surface of the touch sensor, and may determine the vertical direction error based on a magnitude of the generated vertical direction error vector.

The processor may determine that the vertical direction error increases as the magnitude of the vertical direction error vector increases.

In response to the determined vertical direction error being less than or equal to a predetermined threshold value, the processor may estimate blood pressure of the user based on the measured pulse waves, the measured contact force, and the measured contact area.

The processor may calculate a contact pressure between the user and the touch sensor based on the contact force and the contact area, and may estimate the blood pressure of the user by analyzing a change in the pulse waves according to the contact pressure.

In response to the determined vertical direction error exceeding a predetermined threshold value, the processor may generate guide information to guide the user to change the direction of the force to coincide with the vertical direction, may discard measured values of the pulse wave measurer, the contact force measurer and the contact area measurer, and may adjust reliability of a pre-estimated blood pressure estimation value.

According to an aspect of another exemplary embodiment, there is provided a blood pressure measuring method including: sensing contact of a user with a touch sensor; measuring pulse waves from the user; measuring a contact force between the touch sensor and the user by using at least three force sensors; measuring a contact area between the user and the touch sensor; determining a vertical direction error, which indicates a degree of deviation of a direction of force, applied by the user to press the touch sensor, from a vertical direction to a surface of the touch sensor, based on sensor values sensed by the at least three force sensors; and estimating blood pressure of the user according to a determination result of the vertical direction error based on the pulse waves, the contact force, and the contact area.

The measuring the contact force may include measuring the contact force between the user and the touch sensor by adding up or averaging sensor values sensed by the at least three force sensors.

The determining the vertical direction error may include calculating dispersion of the sensor values sensed by the at least three force sensors, and determining the vertical direction error based on the calculated dispersion.

The determining the vertical direction error may include determining that the vertical direction error increases as the calculated dispersion increases.

The determining the vertical direction error may include generating, by using the sensor values sensed by the at least three force sensors, a vertical direction error vector which indicates the direction of the force applied by the user to press the touch sensor, and the degree of the deviation of the direction of force from the vertical direction, and determining the vertical direction error based on a magnitude of the generated vertical direction error vector.

The determining the vertical direction error may include determining that the vertical direction error increases as the magnitude of the vertical direction error vector increases.

The estimating the blood pressure of the user may include, in response to the determined vertical direction error being less than or equal to a predetermined threshold value, estimating the blood pressure of the user based on the measured pulse waves, the measured contact force, and the measured contact area.

The estimating the blood pressure of the user may include, in response to the determined vertical direction error exceeding a predetermined threshold value, generating guide information to guide the user to change the direction of the force to coincide with the vertical direction, discarding measured values of the pulse wave measurer, the contact force measurer, and the contact area measurer, and adjusting reliability of a pre-estimated blood pressure estimation value.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
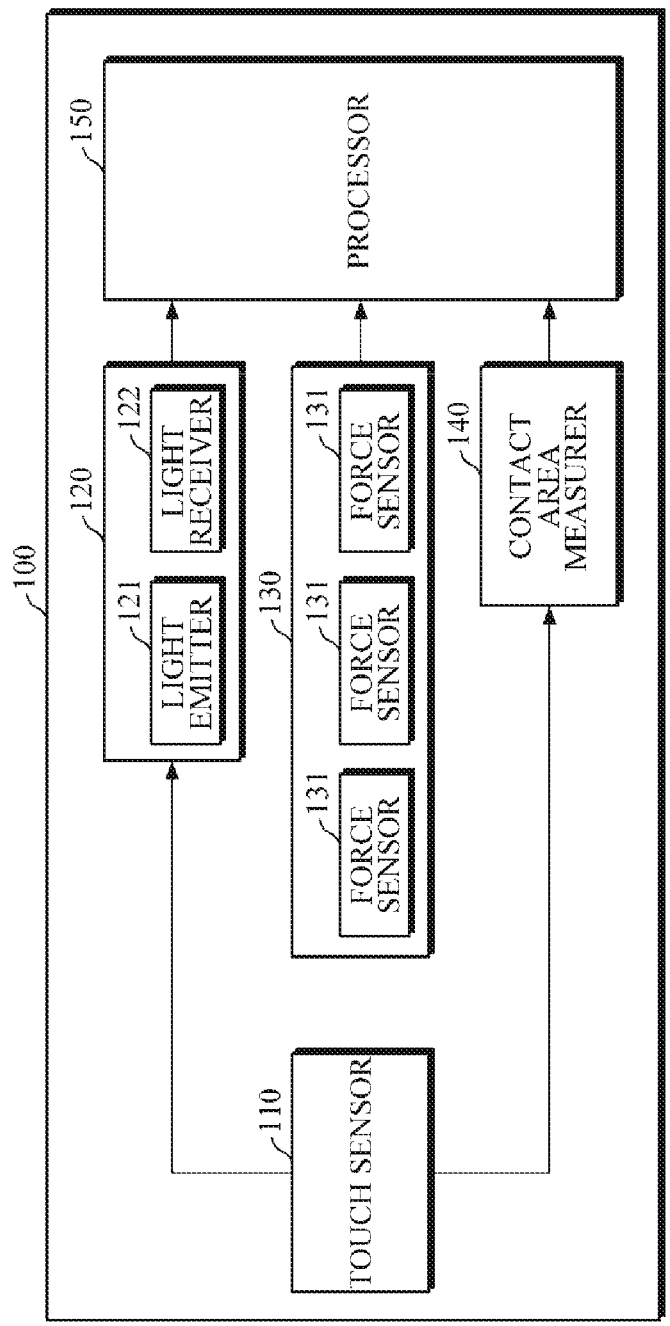
FIG. 1 is a block diagram illustrating an example of a blood pressure measuring apparatus.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Further, components that will be described in the specification are discriminated merely according to functions mainly performed by the components. That is two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented as hardware, software, or a combination of both.

FIG. 1 is a block diagram illustrating an example of a blood pressure measuring apparatus.

The blood pressure measuring apparatus 100 of FIG. 1 may be implemented as a software module or manufactured in the form of a hardware chip to be embedded in various types of electronic devices. In this case, examples of the electronic devices may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 1, the blood pressure measuring apparatus 100 includes a touch sensor 110, a pulse wave measurer 120, a contact force measurer 130, a contact area measurer 140, and a processor 150.

The touch sensor 110 is disposed at an outermost portion of the blood pressure measuring apparatus 100 to sense contact of a user's finger. In one exemplary embodiment, the touch sensor 110 may include a capacitance-type touch sensor.

The touch sensor 110 is disposed above the pulse wave measurer 120, and may have light transmission properties so that the pulse wave measurer 120 may measure a pulse wave signal of a user by transmitting and receiving light to and from the skin of a user touching the touch sensor 110.

A sensor value of the touch sensor 110 may be used to recognize a contact area between the skin of a user and the touch sensor 110, a shape of the contact surface, a center of gravity of the contact surface, a user's fingerprint, and the like.

The pulse wave measurer 120 is disposed below the touch sensor 110, and may measure a pulse wave signal of a user. In this case, the pulse wave signal may include a photoplethysmography signal and the like.

In one exemplary embodiment, when the skin of a user comes into contact with the touch sensor 110, the pulse wave measurer 120 may measure a pulse wave signal of the user by transmitting and receiving light to and from the skin of the user touching the touch sensor 110. To this end, the pulse wave measurer 120 may include a light emitter 121 and a light receiver 122. For example, the pulse wave measurer 120 may be realized as an optical spectrometer.

The light emitter 121 may emit light onto the skin of a user when the user touches the touch sensor 110. The light emitter 121 may include one or more light sources including a light emitting diode (LED), a laser diode, a fluorescent body, or the like.

In one exemplary embodiment, each of the light sources may emit a visible ray, a Near Infrared Ray (NIR), or a Mid Infrared Ray (MIR). However, wavelengths of light emitted from the light sources may vary depending on the purpose of measurement or the types of components to be analyzed. Each of the light sources is not necessarily a single light-emitting body, and may be an array including a plurality of light emitting bodies. Each of the light sources may emit light of the same wavelength, or light of different wavelengths.

The light receiver 122 may receive light reflected or scattered from a user's finger. The light receiver 122 may include one or more photodetectors including a photo diode, a photo transistor (PTr), a charge-coupled device (CCD), or the like. The photodetector is not necessarily a single device, but may be an array including a plurality of devices.

Various numbers and arrangements of light sources and photodetectors may be provided, and the number and the arrangement thereof may vary depending on the purpose of use of the pulse wave measurer 120 and the size and shape of the electronic device including the pulse wave measurer 120.

The contact force measurer 130 may measure a contact force between the skin of a user and the touch sensor 110. To this end, the contact force measurer 130 may include at least three force sensors 131 which are disposed below the touch sensor 110 to surround the pulse wave measurer 120. For example, if the contact force measurer 130 includes three force sensors 131, the three force sensors 131 may be disposed at vertices of a triangle. If the contact force measurer 130 includes four force sensors 131, the four force sensors 131 may be disposed at vertices of a quadrangle. If the contact force measurer 130 includes five force sensors 131, the five force sensors 131 may be disposed at vertices of a pentagon.

In one exemplary embodiment, the contact force measurer 130 may measure a contact force between the skin of a user and the touch sensor 110 by adding up or averaging sensor values sensed by the at least three force sensors 131 when the skin of the user comes into contact with the touch sensor 110. The at least three force sensors 131 may be implemented as piezoelectric force sensors, piezoresistive force sensors, fiberoptic contact-force sensing sensors, and electromagnetic contact force sensing sensors.

The contact area measurer 140 may measure a contact area between the skin of a user and the touch sensor 110. In one exemplary embodiment, the contact area measurer 420 may measure a contact area between the skin of the user and the touch sensor 110 by using sensor values sensed by the touch sensor 110. For example, the contact area measurer 140 may include a capacitive touch sensor to sense the perimeter of a contact area based on capacitance changes of one or more conductors in the blood pressure measuring apparatus 100.

The processor 150 may control the overall operations of the blood pressure measuring apparatus 100.

When the skin of the user comes into contact with the touch sensor 110, the processor 150 may generate guide information for guiding the use to increase or decrease a contact pressure between the skin of the user and the touch sensor 110 for measuring blood pressure, and may provide the generated guide information to a use through an output device. In this case, the output device may include all of a visual output device, an acoustic output device, a tactile output device, and the like.

When the skin of the user comes into contact with the touch sensor 110, the processor 150 may determine a vertical direction error, which indicates a degree of deviation of a direction of force, applied by the skin of a user to press the touch sensor 110, from a vertical direction to the surface of the touch sensor 110, based on the sensor values sensed by the at least three force sensors 131 of the contact force measurer 130.

In one exemplary embodiment, the processor 150 may calculate dispersion of the sensor values sensed by the at least three force sensors 131, and may determine the vertical direction error based on the calculated dispersion. In this case, the processor 150 may determine that the vertical direction error becomes greater as the dispersion increases.

In another exemplary embodiment, by using the sensor values sensed by the at least three force sensors 131, the processor 150 may generate a two-dimensional vertical direction error vector, which indicates a direction of force applied by the skin of the user to press the touch sensor 110, and a degree of deviation of the direction of force from a vertical direction to the surface of the touch sensor 110, and may determine the vertical direction error based on the magnitude of the generated vertical direction error vector. In this case, the processor 150 may determine that the vertical direction error becomes greater as the magnitude of the vertical direction error vector increases.

The processor 150 may perform predetermined functions according to a determination result of the vertical direction error. In this case, the predetermined functions may include estimating blood pressure, generating and outputting guide information, adjusting reliability of a blood pressure estimation value, discarding measured values and performing re-measurement, or the like.

In one exemplary embodiment, the processor 150 may compare the determined vertical direction error with a predetermined threshold value. Upon comparison, in response to the vertical direction error being less than or equal to the predetermined threshold value, the processor 150 may estimate blood pressure of a user based on the pulse waves measured by the pulse wave measurer 120, the contact force measured by the contact force measurer 130, and the contact area measured by the contact area measurer 140. More specifically, in response to the vertical direction error being less than or equal to the predetermined threshold value, the processor 150 may calculate a contact pressure (contact pressure=contact force/contact area) between the skin of the user and the touch sensor 110 based on the contact force measured by the contact force measurer 130 and the contact area measured by the contact area measurer 140. Further, the processor 150 may estimate blood pressure of the user by analyzing a change in pulse waves according to the contact pressure. Blood pressure may include diastolic blood pressure (DBP), systolic blood pressure (SBP), and mean arterial pressure (MAP); and the contact pressure applied to the skin of the user may act as an external pressure on blood vessels. In the case where the contact pressure is lower than the MAP, an elastic restoring force of tissues act to constrict the blood vessels, such that the amplitude of the pulse waves is reduced; in the case where the contact pressure is equal to the MAP, the elastic restoring force of tissues becomes zero, having no effect on the blood vessels, such that the amplitude of the pulse waves reaches its peak value. Further, in the case where the contact pressure is greater than the MAP, the elastic restoring force of tissues act to dilate the blood vessels, such that the amplitude of the pulse waves is reduced. Accordingly, by analyzing the change in pulse waves according to the contact pressure, the processor 150 may estimate, as the MAP, a contact pressure at a peak amplitude of the pulse waves. Further, the processor 150 may estimate, as the systolic blood pressure (SBP), a contact pressure at a point where an amplitude has a value equal to a first percentage (e.g., 0.6) of the peak amplitude; and may estimate, as the diastolic blood pressure (DBP), a contact pressure at a point where an amplitude has a value equal to a second percentage (e.g., 0.7) of the peak amplitude.

In another exemplary embodiment, the processor 150 may compare the determined vertical direction error with a predetermined threshold value. Upon comparison, in response to the vertical direction error exceeding the predetermined threshold value, the processor 150 may generate and output guide information, discard measured values and perform re-measurement, estimate blood pressure and adjust reliability of a blood pressure estimation value, or the like. For example, in response to the vertical direction error exceeding a predetermined threshold value, the processor 150 may generate guide information about a direction of force to be exerted by the user onto the touch sensor 110 so that the direction of force coincides with a vertical direction to the surface of the touch sensor 110. The processor 150 may provide the generated guide information to a user through an output device. In this case, the output device may include all of a visual output device, an acoustic output device, a tactile output device, and the like. In another example, in response to the vertical direction error exceeding the predetermined threshold value, the processor 150 may discard measured values of the pulse wave measurer 120, the contact force measurer 130, and the contact area measurer 140, and may perform re-measurement. In yet another example, even when the vertical direction error exceeds the predetermined threshold value, the processor 150 may estimate blood pressure of a user based on the pulse waves measured by the pulse wave measurer 120, the contact force measured by the contact force measurer 130, and the contact area measured by the contact area measurer 140. In this case, the processor 150 may lower the reliability of a pre-estimated blood pressure estimation value based on the vertical direction error. In addition, the processor 150 may adjust the reliability of a blood pressure estimation value according to the vertical direction error by using a correlation model, which represents a correlation between a predetermined vertical direction error and a change in the reliability of a blood pressure estimation value. In this case, the correlation model may be provided in the form of a mathematical algorithm, but is not limited thereto, and may be provided in the form of a matching table and stored in a storage device.

FIGS. 2A to 2D are exemplary diagrams illustrating comparison of a case where a user presses a touch sensor in a vertical direction with a case where a user presses a touch sensor in a direction other than the vertical direction. In FIGS. 2A to 2D, left portions illustrate a case where a user presses a touch sensor in a vertical direction; and right portions illustrate a case where a user presses a touch sensor in a direction other than the vertical direction.

Figure 2A:
FIGS. 2A, 2B, 2C, and 2D are exemplary diagrams illustrating comparison of a case where a user presses a touch sensor in a vertical direction with a case where a user presses a touch sensor in a direction other than the vertical direction.
Figure 2B:
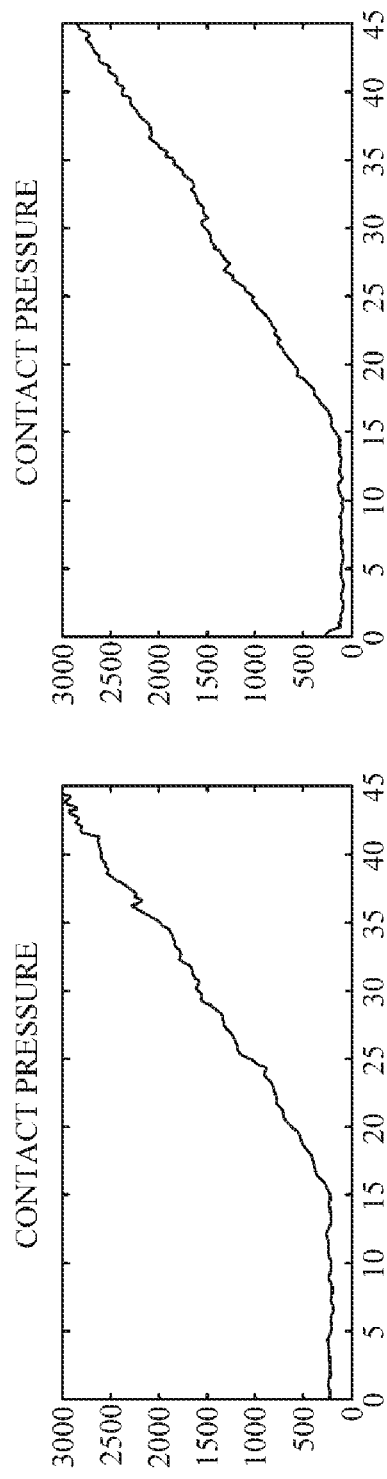
Figure 2C:
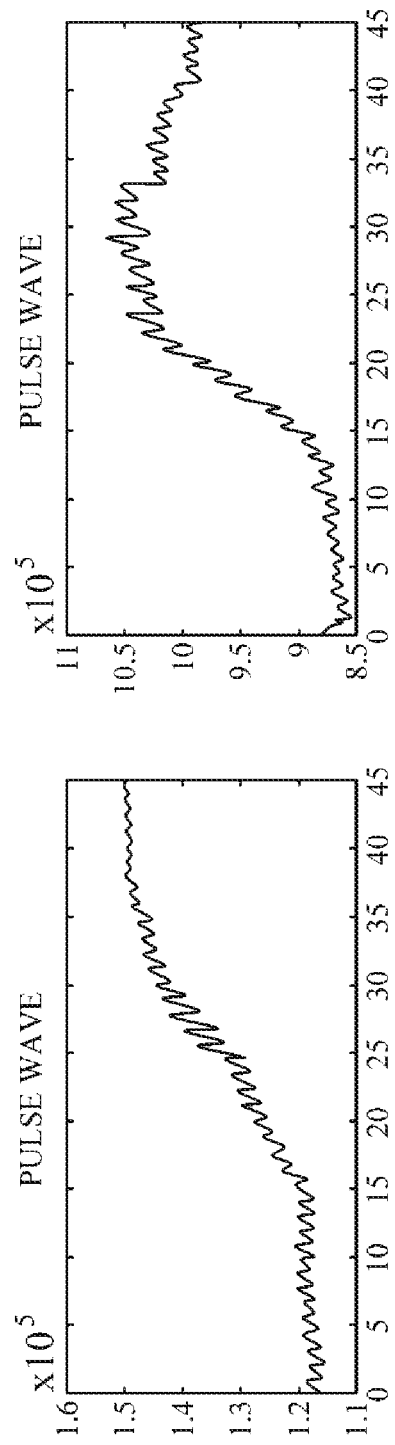
Figure 2D:
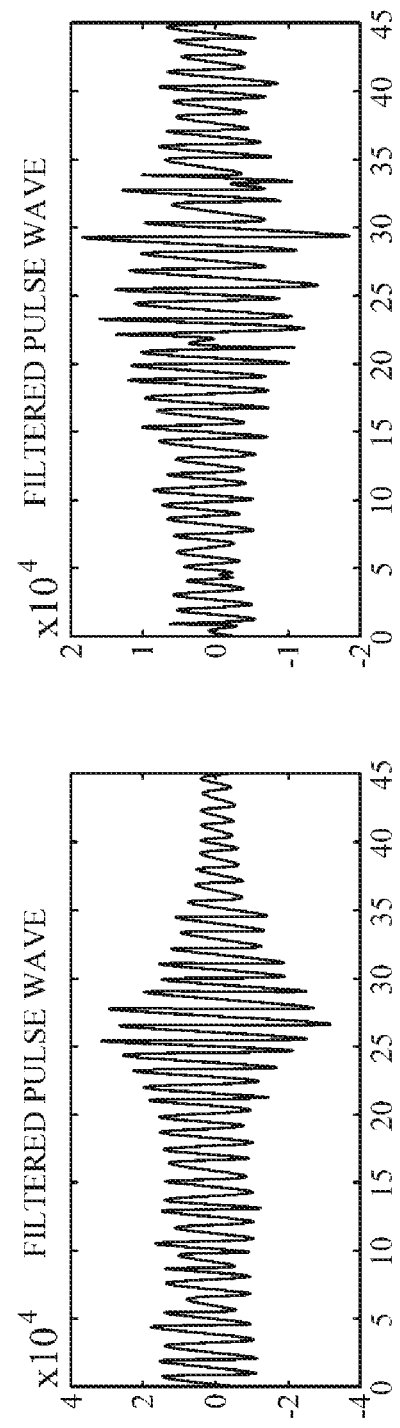

Referring to FIGS. 2A to 2D, upon comparing a case where a user presses a touch sensor in a vertical direction with a case where a user presses a touch sensor in a direction other than the vertical direction, it can be seen that there is no significant difference therebetween (see FIG. 2B). However, upon comparing pulse waves measured in a case where a user presses a touch sensor in a vertical direction with pulse waves measured in a case where a user presses a touch sensor in a direction other than the vertical direction, it can be seen that the pulse waves, measured in a case where a user presses a touch sensor in a vertical direction, show a typical oscillometric waveform in which a maximum pulse wave value is found around the mean blood pressure; by contrast, the pulse waves, measured in a case where a user presses a touch sensor in a direction other than the vertical direction, show an oscillometric waveform in which it is difficult to specify the mean blood pressure, as well as the diastolic blood pressure (DBP) or the systolic blood pressure (SBP) (see FIGS. 2C and 2D).

Accordingly, the blood pressure measuring apparatus 100 may improve accuracy of blood pressure estimation by evaluating a degree of deviation of a direction of force, applied by a user to the touch sensor, from the vertical direction to the surface of the touch sensor, and by inducing the direction of force, applied by the user to the touch sensor, to coincide with the vertical direction to the surface of the touch sensor.

Figure 3:
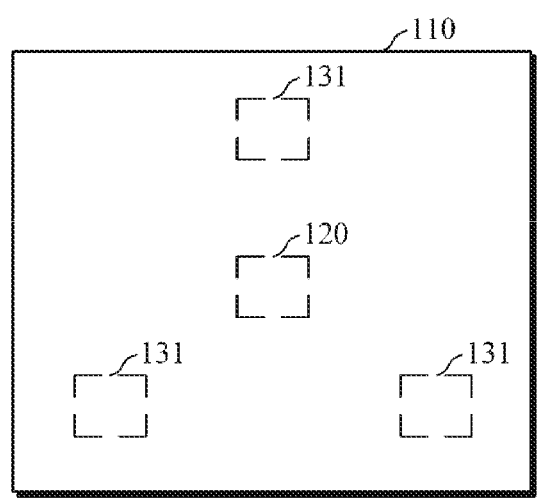
FIG. 3 is an exemplary diagram explaining an arrangement of a pulse wave measurer and force sensors.

FIG. 3 is an exemplary diagram explaining an arrangement of a pulse wave measurer and force sensors. The dotted line in FIG. 3 indicates that the pulse wave measurer 120 and the force sensors 131 are disposed below the touch sensor 110.

Referring to FIG. 3, the pulse wave measurer 120 is disposed at the center of the touch sensor 110, and three force sensors 131 may be disposed at each vertex of a triangle, whose center of gravity lies on a position of the pulse wave measurer 120. In this case, the three force sensors 131 may be disposed on the same plane, and may be disposed at an equal distance from the pulse wave measurer 120, but the arrangement is not limited thereto. For example, the pulse wave measurer 120 may be disposed at a centroid C of the triangle, and x and y coordinates C (x, y) of the centroid C may be obtained as follows:

$$C(x, y) = \left(\frac{x1 + x2 + x3}{3}, \frac{y1 + y2 + y3}{3}\right)$$

wherein, x and y coordinate values of the vertices of the triangle denote $(x_1, y_1)$, $(x_2, y_2)$, and $(x_3, y_3)$.

Figure 4:
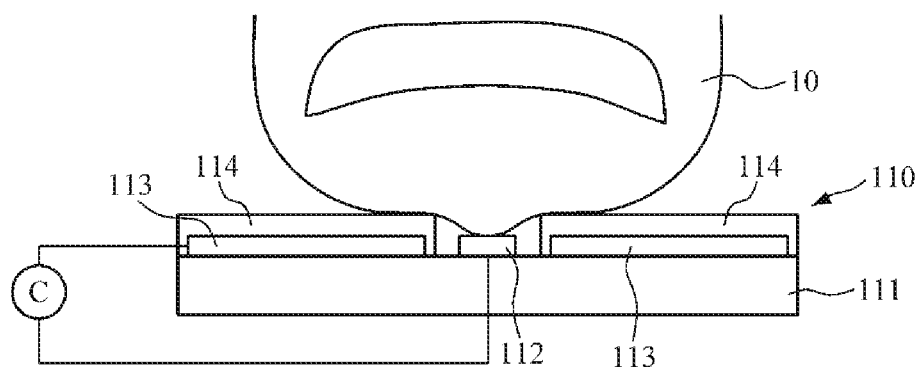
FIG. 4 is a cross-sectional diagram illustrating an example of a touch sensor.

FIG. 4 is a cross-sectional diagram illustrating an example of a touch sensor.

Referring to FIG. 4, the touch sensor 110 may be a capacitance-type touch sensor. The touch sensor 110 includes a transparent substrate 111, a first transparent electrode 112 and a second transparent electrode 113 which are disposed on the transparent substrate 111 and are spaced apart from each other, and a transparent cover 114 which covers a top portion of the second transparent substrate 113 while exposing the first transparent substrate 112.

The transparent substrate 111 may be made of transparent plastic, transparent glass, or the like, to have light transmission and insulation properties. The transparent substrate 111 may support the first transparent electrode 112 and the second transparent electrode 113.

The first transparent electrode 112 and the second transparent electrode 113 may be made of transparent conductive material (e.g., Iridium Tin Oxide (ITO), carbon nanotube, etc.), and may be formed on the transparent substrate 111. The first transparent electrode 112 is disposed at the center of the transparent substrate 111, and the second transparent electrode 113 may be disposed on the periphery of the first transparent electrode 112 while surrounding the first transparent electrode 112. The first transparent electrode 112 and the second transparent electrode 113 may have a predetermined thickness. The first transparent electrode 112 functions as a ground electrode, and the second transparent electrode 113 functions as a sensing electrode.

The transparent cover 114 may be made of transparent plastic, transparent glass, or the like, to have light transmission and insulation properties. The transparent cover 114 may be adhered to the transparent substrate 111 by an adhesive layer while covering the second transparent electrode 113 to protect the second transparent electrode 113.

Although FIG. 4 illustrates an example where the transparent cover 114 covers only the second transparent electrode 113 while exposing the first transparent electrode 112, but the transparent cover 114 is not limited thereto. That is, the transparent cover 114 may be formed to cover the first transparent electrode 113 as well as the second transparent electrode 113, to protect both the first transparent electrode 112 and the second transparent electrode 113.

In the example of FIG. 4, the contact area measurer 140 may measure a contact area of a user's finger 10 as follows.

While a sensing current is supplied to the first transparent electrode 112 and the second transparent electrode 113, when a user touches with a finger a top portion of the transparent cover 114 including the first transparent electrode 112, a change in capacitance between the first transparent electrode 112 and the second transparent electrode 113 may occur by the touch of the finger 10 having capacitance. In this case, a value of change in capacitance may be determined according to a value of a contact area of the finger 10. As the contact area of the finger 10 touching the touch sensor 100 increases, a current flowing to the finger 10 also increases, such that a value of change in capacitance between the first transparent electrode 112 and the second transparent electrode 113 becomes greater. By contrast, as the contact area of the finger 10 touching the touch sensor 110 decreases, a current flowing to the finger 10 also decreases, such that a value of change in capacitance between the first transparent electrode 112 and the second transparent electrode 113 is lowered. Accordingly, by using a predetermined correlation model, which represents a correlation between a contact area of the finger and a value of change in capacitance, the contact area measurer 140 may obtain a contact area of the finger 10 according to the value of change in capacitance. In this case, the correlation model may be provided in the form of a mathematical algorithm, but is not limited thereto, and may be provided in the form of a matching table and stored in a storage device.

Figure 5:
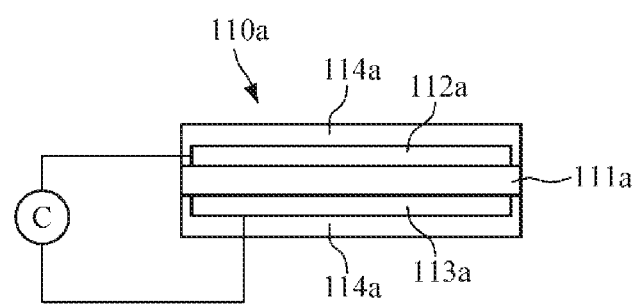
FIG. 5 is a cross-sectional diagram illustrating another example of a touch sensor.

FIG. 5 is a cross-sectional diagram illustrating another example of a touch sensor.

Referring to FIG. 5, a touch sensor 110a includes a transparent substrate 111a, a first transparent electrode 112a and a second transparent electrode 113a which are formed on a top surface and a bottom surface of the transparent substrate 111a respectively, and a transparent cover 114a which covers the first transparent electrode 112a and the second transparent electrode 113a.

The transparent substrate 111a may be made of transparent plastic, transparent glass, or the like, to have light transmission and insulation properties. The transparent substrate 111a may support the first transparent electrode 112a and the second transparent electrode 113a.

The first transparent electrode 112a and the second transparent electrode 113a may be made of transparent conductive material (e.g., Iridium Tin Oxide (ITO), carbon nanotube, etc.), and may be formed on a top surface and a bottom surface of the transparent substrate 111a respectively. The first transparent electrode 112a and the second transparent electrode 113a may have a predetermined thickness. The first transparent electrode 112a functions as a ground electrode, and the second transparent electrode 113a functions as a sensing electrode.

The transparent cover 114a may be made of transparent plastic, transparent glass, or the like, to have light transmission and insulation properties. The transparent cover 114a may cover the first transparent electrode 112a and the second transparent electrode 113a to protect the first transparent electrode 112a and the second transparent electrode 113a.

Although FIG. 5 illustrates an example where the first transparent electrode 112a and the second transparent electrode 113a are formed on one transparent substrate 111a, but the arrangement is not limited thereto. That is, the second transparent electrode 113a may be formed on a separate transparent substrate from the transparent substrate 111a. In this case, the transparent cover 114a covering the second transparent electrode 113a may be omitted.

In the example of FIG. 5, the contact area measurer 140 may measure a contact area of a finger based on a value of change in capacitance which is generated by the touch of the finger between the first transparent electrode 112a and the second transparent electrode 113a.

Figure 6A:
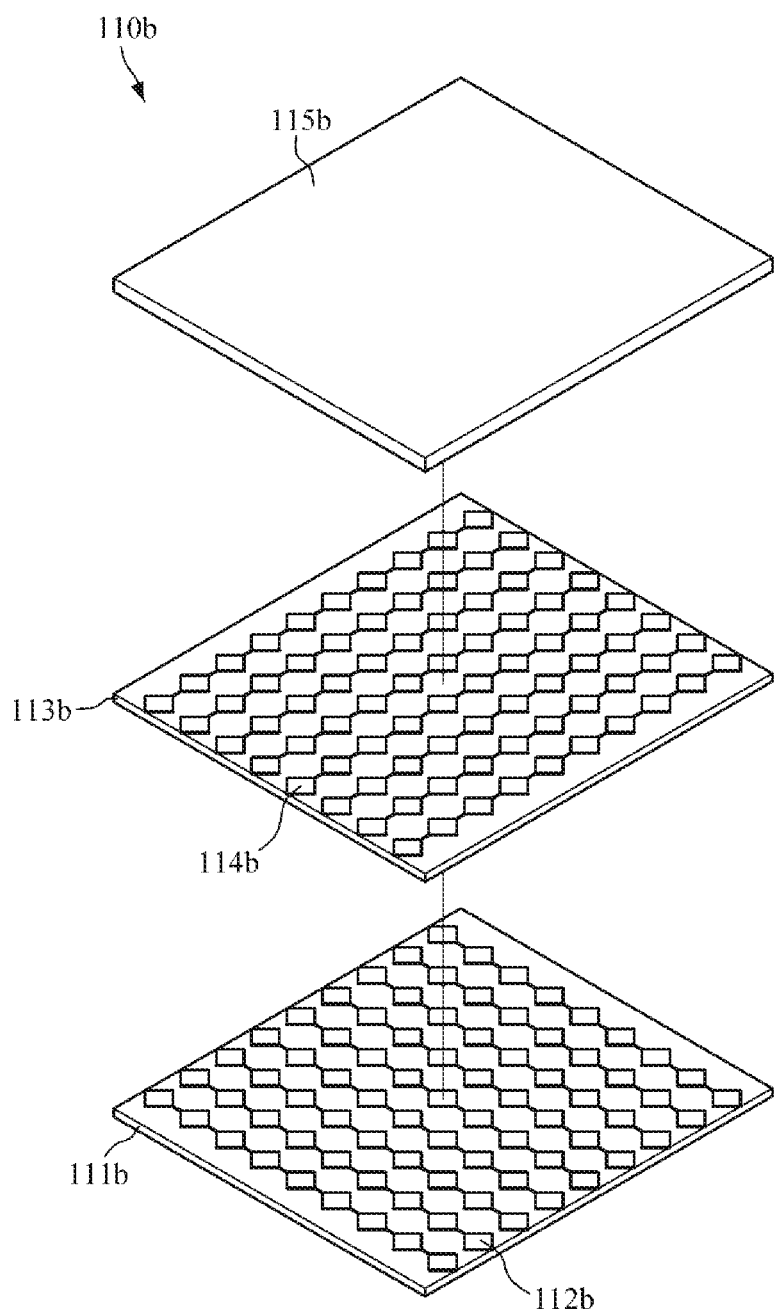
FIG. 6A is an exploded perspective diagram illustrating yet another example of a touch sensor.
Figure 6B:
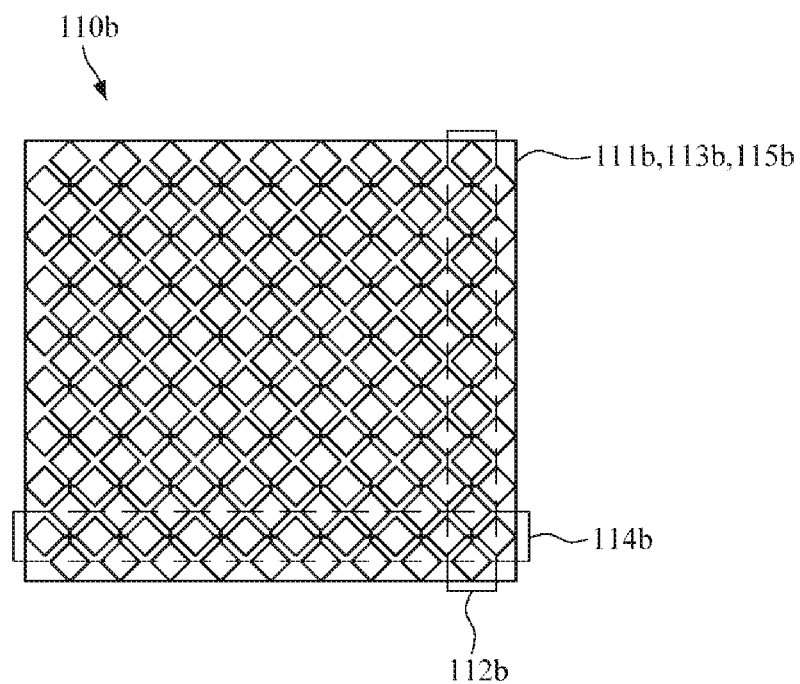
FIG. 6B is a plan view of the touch sensor of FIG. 6A.

FIG. 6A is an exploded perspective diagram illustrating yet another example of a touch sensor, and FIG. 6B is a plan view of the touch sensor of FIG. 6A.

Referring to FIGS. 6A and 6B, the touch sensor 110b includes a transparent substrate 111b, sensing lines 112b arranged in a plurality of columns on the transparent substrate 111b, a transparent insulating layer 113b covering the sensing lines 112b, driving lines 114b arranged in a plurality of rows on the transparent insulating layer 113b, and a transparent cover 115b covering the driving lines 114b.

The transparent substrate 111b may be made of transparent plastic, transparent glass, or the like, to have light transmission and insulation properties. The transparent substrate 111b may support the sensing lines 112b.

The sensing lines 112b and the driving lines 114b may be made of transparent conductive material such as Indium Tin Oxide (ITO), carbon nanotube, and the like. The sensing lines 112b and the driving lines 114b may intersect with each other to form a grid. An intersecting point of the sensing lines 112b and the driving lines 114b may be a pair of coordinates.

The sensing lines 112b may have electrode pads which are connected by a bridge. Here, each of the electrode pads may be formed in a diamond shape. The bridge may have a much narrower width than the electrode pads. In the same manner as the sensing lines 112b, the driving lines 114b may have electrode pads which are connected by a bridge. The sensing lines 112b and the driving lines 114b may be arranged so that the bridges thereof may intersect with each other. Accordingly, two electrode pads of the sensing lines 112b and two electrode pads of the driving lines 114b may be arranged based on intersecting points of the bridges.

The transparent insulating layer 113b may insulate between the sensing lines 112b and the driving lines 114b. The transparent insulating layer 113b may be made of a material having light transmission and insulation properties.

The transparent cover 115b may be made of transparent plastic, transparent glass, or the like, to have light transmission and insulation properties. The transparent cover 115b may protect the driving lines 114b. the transparent cover 115b may be adhered to the transparent insulating layer 113b while covering the driving lines 114b.

In the embodiment of FIGS. 6A and 6B, the contact area measurer 140 may measure a contact area of a user's finger as follows.

While a sensing current is sequentially supplied to the driving lines 114b of the touch sensor 110b, when a user touches with a finger a top portion of the transparent cover 115b, capacitance may be changed at intersecting points touched by the finger, among intersecting points of the sensing lines 112b and the driving lines 114b. In this case, the contact area measurer 140 may obtain coordinates of each of the intersecting points, located at an outermost position, among the intersecting points where capacitance is changed, and may calculate a contact area of the finger based on the obtained coordinate information.

Figure 7:
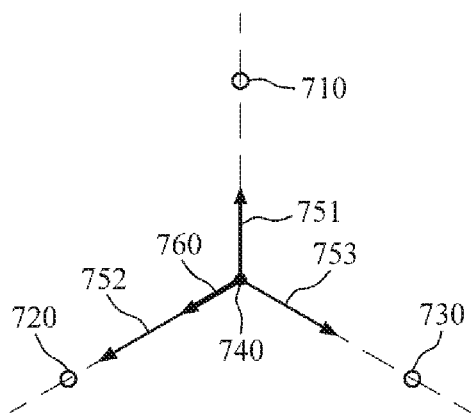
FIG. 7 is an exemplary diagram explaining a method of generating a vertical direction error vector.

FIG. 7 is an exemplary diagram explaining a method of generating a vertical direction error vector. In the exemplary embodiment of FIG. 7, three force sensors are disposed at each vertex of a regular triangle, whose center of gravity lies on a position of a pulse wave measurer. Reference numerals 710, 720, and 730 respectively indicate the positions of the three force sensors, and reference numeral 740 indicates the position of the pulse wave measurer.

Once a user's finger touches the position 740 of the pulse wave measurer of the touch sensor, each of the three force sensors disposed at the positions 710, 720, and 730 may measure a force applied by the finger to the touch sensor.

Assuming that a sensing value sensed by the first force sensor disposed at the position 710 is 10; a sensing value sensed by the second force sensor disposed at the position 720 is 20; and a sensing value sensed by the third force sensor disposed at the position 730 is 14, the processor generates a first vector 751, which is directed from the position 740 to the position 710 and has a magnitude of 10, corresponding to the sensing value of 10 sensed by the first force sensor; generates a second vector 752, which is directed from the position 740 to the position 720 and has a magnitude of 20, corresponding to the sensing value of 20 sensed by the second force sensor; and generates a third vector 753, which is directed from the position 740 to the position 730 and has a magnitude of 14, corresponding to the sensing value of 14 sensed by the third force sensor. Then, the processor may generate a vertical direction error vector 760 by adding up the first vector 751, the second vector 752, and the third vector 753. In this case, the direction of the vertical direction error vector 760 may indicate a direction of force applied by a user's finger to press the touch sensor; and the magnitude of the vertical direction error vector 760 may indicate a degree of deviation of the direction of force, applied by the finger to press the touch sensor, from a vertical direction to the surface of the touch sensor.

Figure 8:
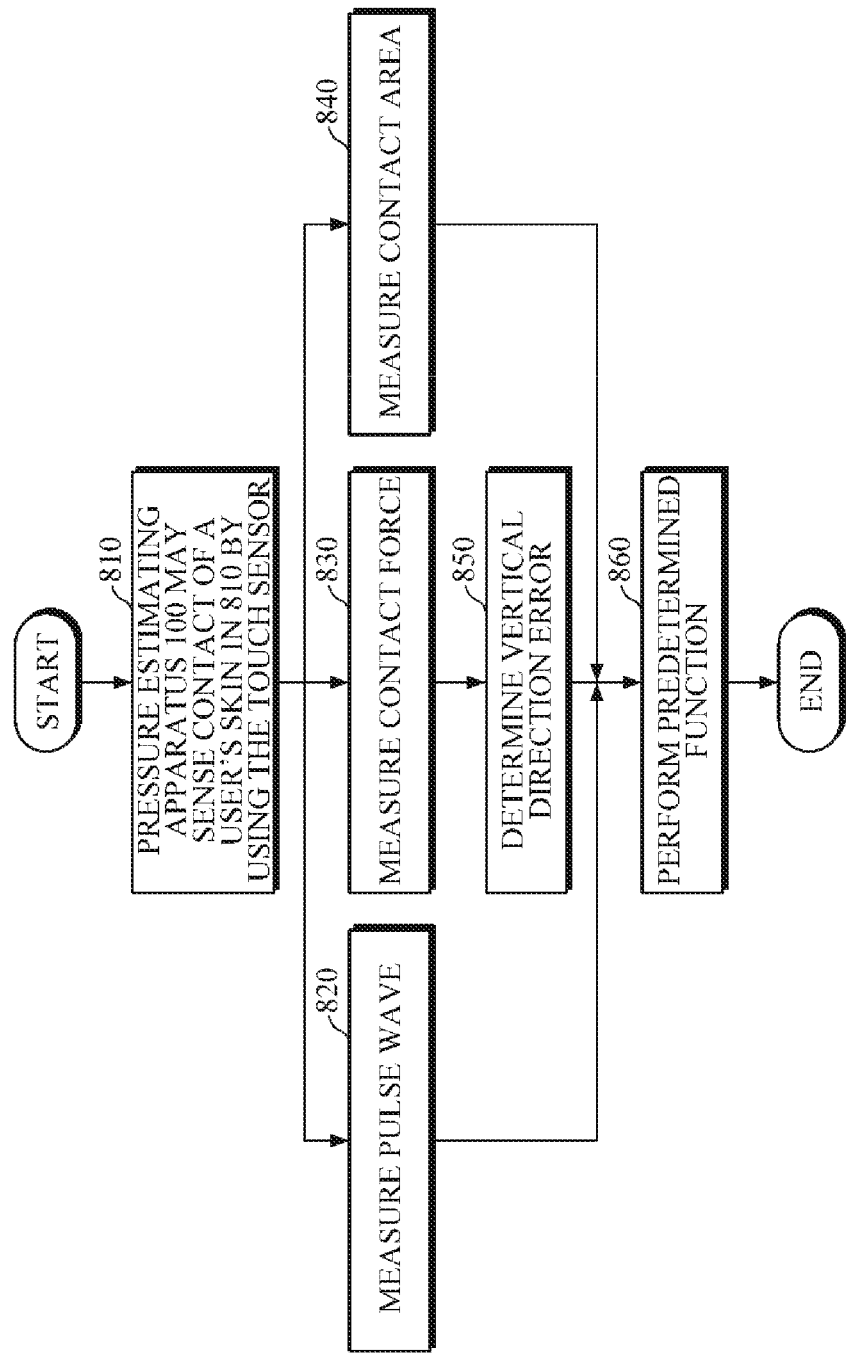
FIG. 8 is a flowchart illustrating an example of a blood pressure estimating method.

FIG. 8 is a flowchart illustrating an example of a blood pressure estimating method. The blood pressure estimating method of FIG. 8 may be performed by the blood pressure estimating apparatus 100 of FIG. 1.

Referring to FIGS. 1 and 8, the blood pressure estimating apparatus 100 may sense contact of a user's skin in operation 810 by using the touch sensor 110.

Upon sensing the contact of the user's skin, the blood pressure estimating apparatus 100 may measure pulse waves of a user by transmitting and receiving light to and from the user's skin touching the touch sensor 110 in operation 820; and may measure a contact force between the user's skin and the touch sensor 110 by using at least three force sensors 131 in operation 830. For example, by adding up or averaging sensor values sensed by the at least three force sensors 131, the blood pressure estimating apparatus 100 may measure the contact force between the user's skin and the touch sensor 110.

The blood pressure estimating apparatus 100 may measure a contact area between the user's skin and the touch sensor 110 by using the sensor values sensed by the touch sensor 110 in operation 840. The method of measuring the contact area between the user's skin and the touch sensor 110 by the blood pressure estimating apparatus 100 is described above with reference to FIGS. 4 to 6B, such that detailed description thereof will be omitted.

By using the sensor values sensed by the at least three force sensors 131, the blood pressure estimating apparatus 100 may determine a vertical direction error which indicates a degree of deviation of a direction of force, applied by the user's skin to press the touch sensor 110, from a vertical direction to the surface of the touch sensor 110 in operation 850. For example, the blood pressure estimating apparatus 100 may calculate dispersion of the sensor values sensed by the at least three force sensors 131, and may determine the vertical direction error based on the calculated dispersion. In this case, the blood pressure estimating apparatus 100 may determine that the vertical direction error becomes greater as the dispersion increases. In another example, by using the sensor values sensed by the at least three force sensors 131, the blood pressure estimating apparatus 100 may generate a vertical direction error vector which indicates a direction of force applied by the skin of the user to press the touch sensor 110, and a degree of deviation of the direction of force from a vertical direction to the surface of the touch sensor 110, and may determine the vertical direction error based on the magnitude of the generated vertical direction error vector. In this case, the blood pressure estimating apparatus 100 may determine that the vertical direction error becomes greater as the magnitude of the vertical direction error vector increases.

The blood pressure estimating apparatus 100 may perform predetermined functions according to a determination result of the vertical direction error in operation 860. In this case, the predetermined functions may include estimating blood pressure, generating and outputting guide information, adjusting reliability of a blood pressure estimation value, discarding measured values and performing re-measurement, or the like.

Figure 9:
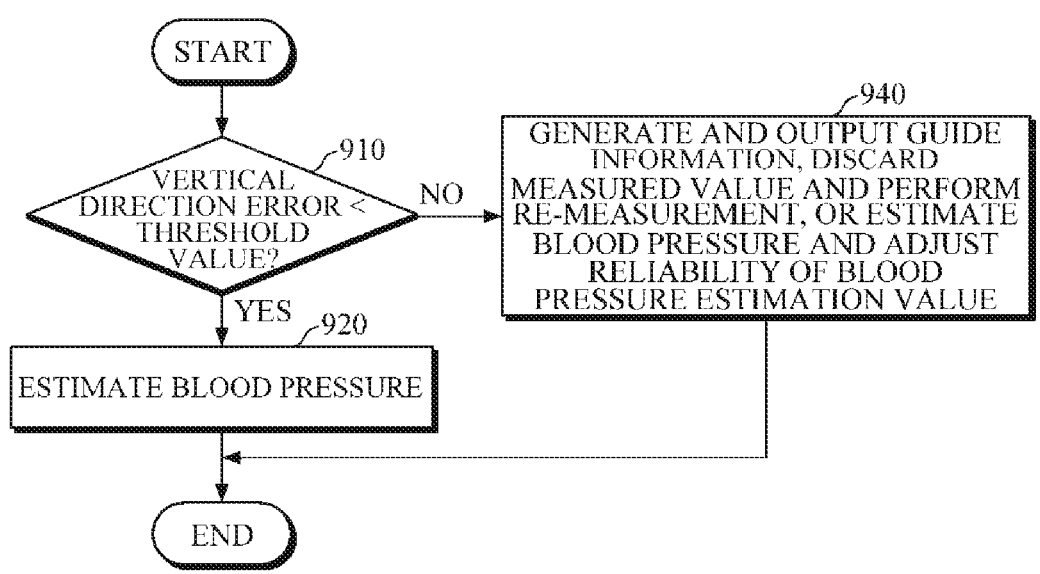
FIG. 9 is a flowchart illustrating an example of a method of performing functions according to a determination result of a vertical direction error.

FIG. 9 is a flowchart illustrating an example of a method of performing functions according to a determination result of a vertical direction error, which may be an example of the operation 860 of FIG. 8.

Referring to FIGS. 1 and 9, the blood pressure estimating apparatus 100 may compare a vertical direction error with a predetermined threshold value in operation 910. In this case, the predetermined threshold value may be preset according to performance and purpose of use of the blood pressure estimating apparatus 100.

In response to the vertical direction error being less than or equal to the predetermined threshold value, the blood pressure estimating apparatus 100 may estimate blood pressure of a user based on the measured pulse waves, the measured contact force, and the measured contact area in operation 920. For example, in response to the vertical direction error being less than or equal to the predetermined threshold value, the blood pressure estimating apparatus 100 may calculate a contact pressure (contact pressure=contact force/contact area) between the skin of the user and the touch sensor 110 based on the measured contact force and the measured contact area, and may estimate blood pressure of the user by analyzing a change in pulse waves according to the contact pressure.

In response to the vertical direction error exceeding the predetermined threshold value, the blood pressure estimating apparatus 100 may generate and output guide information, discard measured values and perform re-measurement, estimate blood pressure and adjust reliability of a blood pressure estimation value, or the like in operation 940. For example, in response to the vertical direction error exceeding the predetermined threshold value, the blood pressure estimating apparatus 100 may generate guide information for guiding a direction of force, applied by the skin of the user to press the touch sensor 110, to coincide with a vertical direction to the surface of the touch sensor 110, and may provide the generated guide information to a user through an output device. In another example, in response to the vertical direction error exceeding the predetermined threshold value, the blood pressure estimating apparatus 100 may discard measured values (e.g., the measured pulse waves, the measured contact force, the measured contact area, etc.), and may perform re-measurement. In yet another example, even when the vertical direction error exceeds the predetermined threshold value, the blood pressure estimating apparatus 100 may measure blood pressure of the user based on the measured pulse waves, the measured contact force, and the measured contact area. In this case, the blood pressure estimating apparatus 100 may adjust reliability of a pre-estimated blood pressure estimation value based on the vertical direction error.

Figure 10:
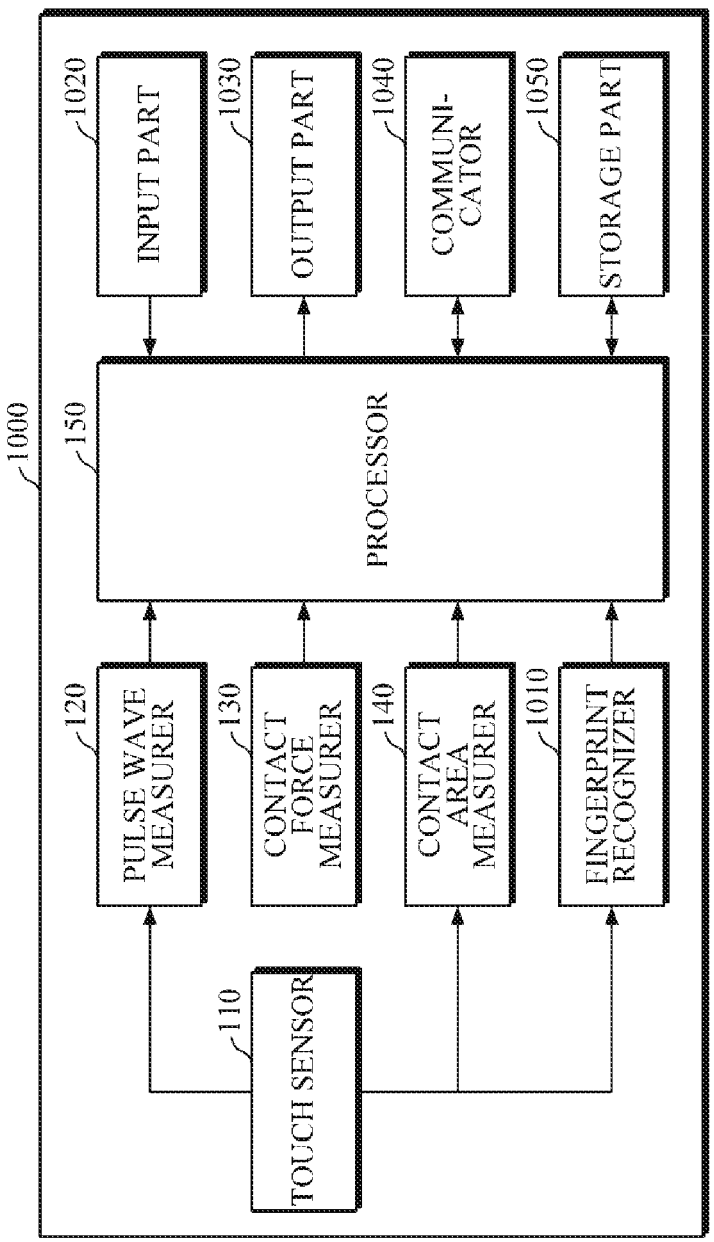
FIG. 10 is a block diagram illustrating another example of a blood pressure measuring apparatus.

FIG. 10 is a block diagram illustrating another example of a blood pressure measuring apparatus.

Referring to FIG. 10, the blood pressure measuring apparatus 1000 includes a touch sensor 110, a pulse wave measurer 120, a contact force measurer 130, a contact area measurer 140, a processor 150, a fingerprint recognizer 1010, an input part (e.g., an input interface) 1020, an output part (e.g., an output interface) 1030, a communicator (e.g., a communication interface) 1040, and a storage part (e.g., a storage or memory) 1050. Here, the touch sensor 110, the pulse wave measurer 120, the contact force measurer 130, the contact area measurer 140, and the processor 150 are described above with reference to FIG. 1, such that detailed description thereof will be omitted.

The fingerprint recognizer 1010 may recognize a fingerprint of a contacting portion of a user's skin touching the touch sensor 110. In one exemplary embodiment, the fingerprint recognizer 1010 may recognize a ridge and a valley of the contacting portion of a finger by using sensor values sensed by the touch sensor 110, and may recognize a fingerprint of a contacting portion of the user's skin based on the recognized ridge and valley. In this case, the processor 150 may identify a user by comparing the recognized fingerprint with pre-stored fingerprint data, and may store blood pressure information, measured for the user, in the storage part 1050 as information of the user.

The input part 1020 may receive input of various operation signals from a user. In one embodiment, the input part 1020 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The input part 1020 may receive input of user-related information. In this case, the user-related information may include height, weight, age, and the like. Based on the input user-related information, the processor 150 may correct blood pressure. A suitable blood pressure estimation correlation model may be stored for each user in the storage part 1050, and the processor 150 may correct blood pressure by selecting a blood pressure correlation model, which is suitable for a corresponding user, from the storage part 1050.

The output part 1030 may output data input by a user, data obtained or processed by blood pressure measuring apparatus 1000, and information required for processing data of the blood pressure measuring apparatus 1000, and the like. In one embodiment, the output part 1030 may output the data input by a user, the data obtained or processed by blood pressure measuring apparatus 1000, and the information required for processing data of the blood pressure measuring apparatus 1000, and the like by using at least one of an acoustic method, a visual method, and a tactile method. To this end, the output part 1030 may include a display, a speaker, a vibrator, and the like.

The communicator 1040 may perform communication with an external device. For example, the communicator 1040 may transmit, to the external device, the data input by a user, the data obtained or processed by blood pressure measuring apparatus 1000, and the information required for processing data of the blood pressure measuring apparatus 1000, and the like; or may receive, from the external device, various data useful for estimation of blood pressure.

In this case, the external device may be medical equipment using the data input by a user, the data obtained or processed by blood pressure measuring apparatus 1000, and the information required for processing data of the blood pressure measuring apparatus 1000, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 1040 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

The storage part 1050 may store programs or commands for operation of the blood pressure measuring apparatus 1000, and may store data input to and output from the blood pressure measuring apparatus 1000. Further, the storage part 1050 may store the data input by a user, the data obtained or processed by blood pressure measuring apparatus 1000, and the information required for processing data of the blood pressure measuring apparatus 1000, and the like.

The storage part 1050 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the blood pressure measuring apparatus 1000 may operate an external storage medium, such as web storage and the like, which performs a storage function of the storage part 1050 on the Internet.

Figure 11:
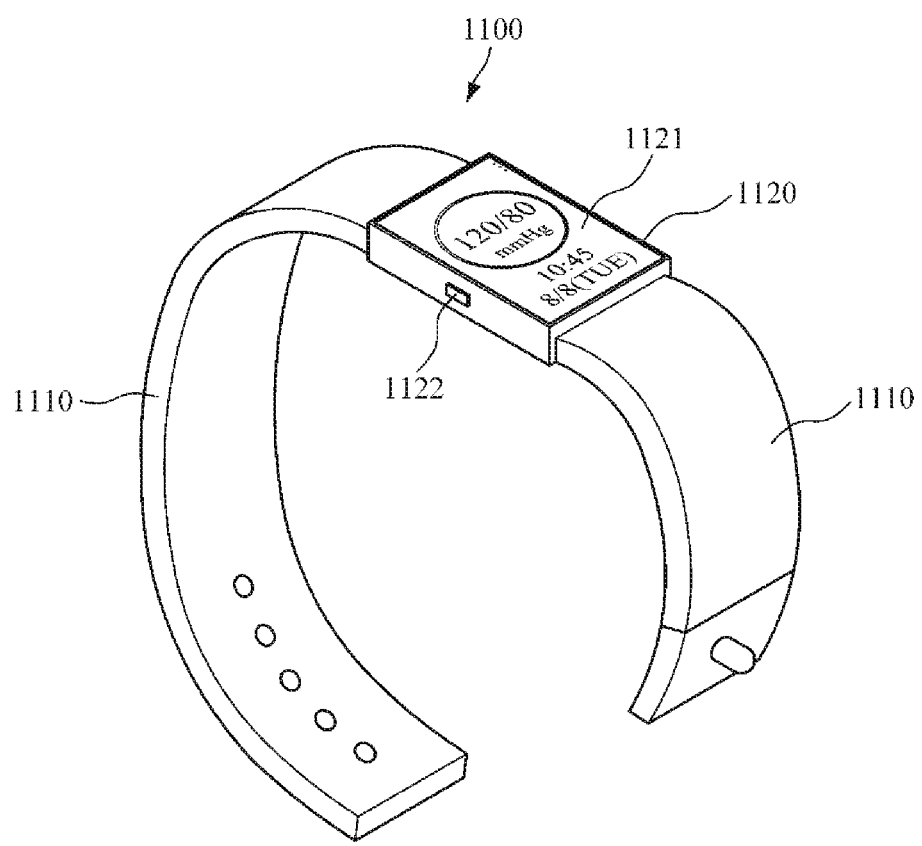
FIG. 11 is a diagram illustrating a wrist-type wearable device.

FIG. 11 is a diagram illustrating a wrist-type wearable device.

Referring to FIG. 11, the wrist-type wearable device 1100 includes a strap 1110 and a main body 1120.

The strap 1110 may be connected at both sides of the main body 1120, and both ends of the strap 1110 may be detachably fastened to each other, or may be integrally formed as a smart band strap. The strap 1110 may be made of a flexible material to wrap around a user's wrist so that the main body 1120 may be worn around a user's wrist.

The main body 1120 may include the above-described blood pressure estimating apparatuses 100 and 1000. Further, the main body 1120 may include a battery which supplies power to the wrist-type wearable device 1100 and the blood pressure estimating apparatuses 100 and 1000.

The touch sensor may be mounted at the top of the main body 1120 to be exposed so that a user's finger may easily touch the touch sensor. However, the touch sensor is not limited thereto, and may be mounted at the strap 1110.

The wrist-type wearable device 1100 may further include a display 1121 and an input part 1122 which are mounted at the main body 1120. The display 1121 may display data processed by the wrist-type wearable device 1100 and the blood pressure estimating apparatuses 100 and 1000, processing result data, and the like thereof. The input part 1122 may receive input of various operation signals from a user.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A blood pressure measuring apparatus, comprising:
   a touch sensor configured to measure a contact area between a user and the touch sensor;
   a contact force measurer comprising at least three force sensors disposed at, at least three different positions, and configured to measure a contact force between the touch sensor and the user by using the at least three force sensors,
   wherein the least three force sensors comprises
      a first force sensor disposed at a first position and configured to measure a first vector directed from a centroid of the at least three different positions of the least three force sensors to the first position,
      a second force sensor disposed at a second position and configured to measure a second vector directed from the centroid to the second position, and
      a third force sensor disposed at a third position and configured to measure a third vector directed from the centroid to the third position;
   a photoplethysmography (PPG) sensor disposed at the centroid of the at least three different positions of the at least three force sensors, and configured to obtain a PPG signal while the contact force is being applied between the touch sensor and the user; and
   a processor configured to determine a vertical direction error which indicates a degree of deviation of a direction of the contact force from a vertical direction to a surface of the touch sensor, by adding the first vector, the second vector and the third vector of the first force sensor, the second force sensor, and the third force sensor, and in response to the vertical direction error being less than or equal to a predetermined threshold value, activate the PPG sensor located at the centroid of the first force sensor, the second force sensor, and the third force sensor, and estimate blood pressure based on the PPG signal; and a ratio of the contact force to the contact area.

2. The blood pressure measuring apparatus of claim 1, wherein the at least three force sensors are disposed at an equal distance from the PPG sensor.

3. The blood pressure measuring apparatus of claim 1, wherein the contact force measurer is further configured to measure the contact force between the user and the touch sensor by adding up or averaging the first vector, the second vector, and the third vector.

4. The blood pressure measuring apparatus of claim 1, wherein the touch sensor comprises:
- a transparent substrate;
- a first transparent electrode and a second transparent electrode that are disposed on the transparent substrate and are spaced apart from each other; and
- a transparent cover that covers a top portion of the second transparent electrode while exposing the first transparent electrode.

5. The blood pressure measuring apparatus of claim 1, wherein the processor is further configured to generate a vertical direction error vector, which indicates the direction of the contact force applied by the user to press the touch sensor, and the degree of deviation of the direction of the contact force from the vertical direction, and determine the vertical direction error based on a magnitude of the generated vertical direction error vector.

6. The blood pressure measuring apparatus of claim 1, wherein the touch sensor comprises:
- a transparent substrate;
- a first transparent electrode and a second transparent electrode that are disposed on a top surface and a bottom surface of the transparent substrate, respectively, so that the transparent substrate is placed between the first transparent electrode and the second transparent electrode; and
- a transparent cover that covers an outer surface of the first transparent electrode and an outer surface of the second transparent electrode.

7. The blood pressure measuring apparatus of claim 1, wherein the processor is further configured to estimate the blood pressure of the user by analyzing a change in the PPG signal according to a contact pressure that corresponds to the ratio of the contact force to the contact area.

8. The blood pressure measuring apparatus of claim 1, wherein in response to the determined vertical direction error exceeding the predetermined threshold value, the processor is further configured to generate guide information to guide the user to change the direction of the force to coincide with the vertical direction, and discard the PPG signal that is obtained at a time when the contact force is applied, and adjust reliability of the estimated blood pressure.

9. A blood pressure measuring method, comprising:
sensing contact of a user with a touch sensor;
measuring a contact force between the touch sensor and the user by using at least three force sensors disposed at, at least three different positions, wherein the at least three force sensors comprises a first force sensor, a second force sensor, and a third force sensor, and wherein the measuring the contact force comprises:
measuring, by the first force sensor disposed at a first position, a first vector directed from a centroid of the at least three different positions of the least three force sensors to the first position,
measuring, by the second force sensor disposed at a second position, a second vector directed from the centroid to the second position; and
measuring, by the third force sensor disposed at a third position, a third vector directed from the centroid to the third position;
measuring a photoplethysmography (PPG) signal from the user by a PPG sensor disposed at the centroid of the at least three different position of the at least three force sensors, while the contact force is being applied between the touch sensor and the user;
measuring a contact area between the user and the touch sensor;
determining a vertical direction error which indicates a degree of deviation of a direction of the contact force from a vertical direction to a surface of the touch sensor, by adding the first vector, the second vector and the third vector of the first force sensor, the second force sensor, and the third force sensor; and
in response to the vertical direction error being less than or equal to a predetermined threshold value, estimating blood pressure of the user according to a determination result of the vertical direction error based on the PPG signal of the PPG sensor located at the centroid of the first force sensor, the second force sensor, and the third force sensor, and a ratio of the contact force to the contact area.

10. The blood pressure measuring method of claim 9, wherein the vertical direction error increases as the degree of deviation increases.

11. The blood pressure measuring method of claim 9, wherein the vertical direction error increases as a magnitude of a combination of the first vector, the second vector, and the third vector.

12. The blood pressure measuring method of claim 9, wherein the estimating the blood pressure of the user comprises, in response to the vertical direction error exceeding the predetermined threshold value, generating guide information to guide the user to change the direction of the contact force to coincide with the vertical direction, discarding the PPG signal that is obtain at a time when the contact force is applied, and adjusting reliability of the estimated blood pressure.

* * * * *